United States Patent
Telfer et al.

(10) Patent No.: US 10,655,101 B2
(45) Date of Patent: May 19, 2020

(54) METHODS OF IN VITRO OOCYTE DEVELOPMENT

(71) Applicant: The University Court of the University of Edinburgh, Edinburgh (GB)

(72) Inventors: Evelyn Elizabeth Telfer, Edinburgh (GB); Marie McLaughlin, Edinburgh (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 441 days.

(21) Appl. No.: 15/513,628

(22) PCT Filed: Sep. 24, 2015

(86) PCT No.: PCT/GB2015/052769
§ 371 (c)(1),
(2) Date: Mar. 23, 2017

(87) PCT Pub. No.: WO2016/046557
PCT Pub. Date: Mar. 31, 2016

(65) Prior Publication Data
US 2017/0283771 A1 Oct. 5, 2017

(30) Foreign Application Priority Data
Sep. 24, 2014 (GB) .................................. 1416858.7

(51) Int. Cl.
*C12N 5/0735* (2010.01)
*C12N 5/075* (2010.01)
*C12N 5/071* (2010.01)
*C12N 5/00* (2006.01)
*A01N 1/02* (2006.01)

(52) U.S. Cl.
CPC .......... *C12N 5/0611* (2013.01); *C12N 5/0037* (2013.01); *C12N 5/0081* (2013.01); *C12N 5/0609* (2013.01); *C12N 5/0682* (2013.01); *A01N 1/0268* (2013.01); *C12N 5/0018* (2013.01); *C12N 2500/25* (2013.01); *C12N 2500/38* (2013.01); *C12N 2500/90* (2013.01); *C12N 2501/105* (2013.01); *C12N 2501/11* (2013.01); *C12N 2501/125* (2013.01); *C12N 2501/16* (2013.01); *C12N 2501/31* (2013.01); *C12N 2501/392* (2013.01); *C12N 2502/243* (2013.01); *C12N 2527/00* (2013.01)

(58) Field of Classification Search
None
See application file for complete search history.

(56) References Cited

U.S. PATENT DOCUMENTS

2007/0010013 A1* 1/2007 Bukovsky ............ C12N 5/0604
435/366
2016/0237402 A1* 8/2016 Tilly ...................... A61K 35/54

OTHER PUBLICATIONS

Telfer et al., Human Repro., 23(5):1151-1158 (2008) (Year: 2008).*
Hanna et al., Fertil. Steril., 101(1):20-30 (2014) (Year: 2014).*
UCSF (FSH, www.ucsfbenioffchildrens.org/tests/003710.html, 2012 (Accessed Aug. 7, 2019) (Year: 2012).*
Garcia-Campayo et al., Endocrinol., 142(42):5203-5211 (2001) (Year: 2001).*
Ramesh et al., Adv. Biol. Res. 1(1-2):29-33 (2007) (Year: 2007).*
Dunlop et al., Maturitas, 76:279-283 (2013) (Year: 2013).*
Gutierrez et al., BOR, 62:1322-1328 (2000) (Year: 2000).*
Sanchez et al., Human Reprod. Update, 20(2):217-230 (2014) (Year: 2014).*
Smitz et al., Human Reprod. Update, 16(4):395-414 (2010) (Year: 2010).*
Telfer et al., Abstract 0-148 (2008) (Year: 2008).*
Telfer Presentation (2009) (Year: 2009).*
Telfer et al., Fertil Steril., 99(6): 1523-1533 (2013) (Year: 2013).*
Grieve et al., Maturitas 82 278-281 (2015) (Year: 2015).*
White et al., Nat Med., 18(3):413-421 (2012) (Year: 2012).*
Woods et al., Reprod. Sci., 20(1):7-15 (2013) (Year: 2013).*
Telfer et al., Hum. Reprod., 23(5):1151-1158 (2008) (Year: 2008).*
R.A. Anderson et al: "The immature human ovary shows loss of abnormal follicles and increasing follicle developmental competence through childhood and adolescence"; Human Reproduction; Oct. 17, 2013; pp. 97-106; vol. 29, No. 1; Oxford University Press; United Kingdom.
Marie McLaughlin et al: "Oocyte development in bovine primordial follicles is promoted by activin and FSH within a two-step serum-free culture system"; Reproduction Research; Mar. 4, 2010; pp. 971-978; vol. 139; Oxford University Press, United Kingdom.
Evelyn Telfer: "Novel systems and factors to improve oocyte quality in vitro"; Mar. 29, 2012; URL:https://www.eshre.ue/~/media/sitecore-files/SIGs/Embryology/Archiv/Stresa-2012/Telfer2.pdf?la=en; The University of Edinburgh, United Kingdom.
Talal El-Henvawy et al: "Synergism Between FSH and Activin in the Regulation of Proliferating Cell Nuclear Antigen (PCNA) and Cyclin D2 Expression in Rat Granulosa Cells"; Endocrinology; Oct. 1 2001; pp. 4357-4362; vol. 142 (10); The Endocrine Society, U.S.A.

(Continued)

*Primary Examiner* — Thomas J. Visone
(74) *Attorney, Agent, or Firm* — Dickinson Wright PLLC

(57) ABSTRACT

Methods of preparing ovarian tissue for primordial follicle growth are presented comprising the steps: providing an ovarian tissue sample comprising cortical tissue and stromal tissue; removing damaged tissue from the ovarian tissue sample where present; removing excess stromal tissue from the ovarian tissue sample where present; and then mechanically stretching the ovarian tissue sample along at least one dimension of the ovarian tissue sample, such that the size of the ovarian tissue sample along the at least one dimension is increased by at least 10%. Methods of growing viable oocyte in vitro, and methods of preparing individual ovarian follicles for growth are also presented.

14 Claims, 3 Drawing Sheets

(56) References Cited

OTHER PUBLICATIONS

Seung-Hee Song et al: "Characterization of Porcine Multipotent Stem/Stromal Cells Derived from Skin, Adipose and Ovarian Tissues and Their Differentiation In Vitro into Putative Oocyte-Like Cells"; Stem Cells and Development; 2011; pp. 1359-1370; vol. 20 No. 8; Mary Ann Liebert, Inc.; New York, U.S.A.

Evelyn E. Telfer et al: "Strategies to support human oocyte development in vitro"; International Journal of Developmental Biology; Oct. 11, 2012; pp. 901-907 vol. 56; UBC Press; Spain.

\* cited by examiner

METHODS OF IN VITRO OOCYTE DEVELOPMENT

CROSS-REFERENCE TO RELATED APPLICATIONS

The present application is a 35 U.S.C. Section 371 national stage filing of International Patent Application No. PCT/GB2015/052769, filed 24 Sep. 2015, and through which priority is claimed to United Kingdom Patent Application No. 1416858.7, filed 24 Sep. 2014, the disclosures of which are incorporated herein by reference in their entireties.

The present invention relates to oocytes and methods of in vitro oocyte development.

BACKGROUND OF THE INVENTION

The ability to grow large mammalian oocytes from the earliest follicular stages through to maturation and fertilisation in vitro would not only provide a model system to study the process of oocyte development in these species, it could potentially revolutionise fertility preservation practice in humans and animal production systems for cattle, for example. The production of live offspring from oocytes grown in vitro from the primordial stage has only been achieved in mice (Eppig and O'Brien 1996; O'Brien et al., 2003). This demonstration has led to a step wise development of similar culture systems for humans and domestic animals. Each of these systems support different stages of oocyte development.

In principle, primordial follicles are isolated from cortical tissue (often taken via biopsy), and grown into oocytes, which can then be fertilised. However, the different systems in the art are not necessarily designed to work together, and, therefore, such systems may not be compatible or may not provide a useful or efficient method of producing in vitro viable and healthy oocytes for later fertilisation, ultimately resulting in live offspring.

In addition, developing in vitro maturation systems for the development of primordial follicles into oocytes in larger mammals, such as human, bovine or ovine, for example, has been more difficult to achieve because of differences in scale of timing and size between rodents and larger mammals (Telfer and McLaughlin, 2012). These differences have led to low yields of viable and healthy oocytes from these systems.

Therefore, it is an object of at least one aspect of the present invention to provide a viable and practicable method of developing viable and healthy larger mammalian oocytes from primordial follicles.

STATEMENTS OF THE INVENTION

According to a first aspect of the invention, there is provided a method of preparing ovarian tissue for primordial follicle growth comprising the steps:
  providing an ovarian tissue sample comprising cortical tissue and stromal tissue;
  removing damaged tissue from the ovarian tissue sample where present;
  removing excess stromal tissue from the ovarian tissue sample where present; and then
  mechanically stretching the ovarian tissue sample along at least one dimension of the ovarian tissue sample, such that the size of the ovarian tissue sample along the at least one dimension is increased by at least 10%.

Typically, the ovarian tissue sample is taken from a larger mammal. For example, the ovarian tissue sample may be in the form of a biopsy sample taken from the ovary of a pig, cow, sheep or human. The ovarian tissue sample may be a human tissue sample.

The ovarian tissue sample used in the method of the present aspect of the invention may be the whole or part of an original ovarian tissue sample. For example, in embodiments where the ovarian tissue sample is in the form of a biopsy sample, the ovarian tissue sample used in the method of the present aspect of the invention may be the whole biopsy sample or a fragment or subsection thereof.

Where the ovarian tissue sample has been obtained via biopsy, the ovarian tissue sample may comprise damaged tissue. By the term "damaged tissue" we refer to tissue, vessels and/or ducts that may be hemorrhaging, or that may have been punctured or torn during biopsy, when the ovarian tissue sample was cut away from the parent tissue.

Damaged tissue may release enzymes, hormones or other factors that may inhibit primordial follicle growth. Therefore, the step of removing damaged tissue from the ovarian tissue sample prevents or limits contamination of the undamaged tissue by inhibiting factors that may result in the inhibition of growth of primordial follicles.

By "mechanically stretching" we refer to the application of physical force to the ovarian tissue sample in a direction away from an anchor point along the at least one dimension of the ovarian tissue sample to thereby stretch the tissue. For example, the ovarian tissue sample may comprise fibres generally running parallel to the at least one dimension, and the said fibres may move past each other in a direction parallel to the at least one dimension upon application of the physical force in a direction parallel to the at least one dimension, to thereby increase the size of the ovarian tissue sample along the at least one dimension.

By the term "primordial follicles" we refer to immature follicles that have not as yet been activated to grow. Such follicles are commonly referred to in the art as being in the "primordial stage" or "primordial state".

Methods for growing ovarian follicles in vitro known in the art typically suffer from minimal follicle activation, and, therefore, the number of growing ovarian follicles is low, growth rates of the few ovarian follicles that are growing is slow, and the resulting oocytes are of limited viability and health. As such, these methods are inefficient and of limited use for producing viable, healthy oocytes.

The inventors have surprisingly found that the step of mechanically stretching the ovarian tissue sample increases the number of viable and healthy follicles that can be subsequently observed growing within the cortical tissue.

Typically, ovarian tissue comprises dense fibres, and the action of stretching the ovarian tissue sample may loosen or reduce the density of these fibres. Loosening or reducing the density of the ovarian tissue fibres may weaken the interactions between fibres and thereby increase the distance between fibres. Accordingly, the step of mechanically stretching the ovarian tissue sample may allow exogenous species such as media, proteins, enzymes or cells to permeate between the fibres into the ovarian tissue more readily.

In addition, the cortical tissue of the ovarian tissue sample often comprises primordial follicles and these primordial follicles within the cortical tissue may be densely packed within the cortical tissue. For example, the density of primordial follicles may be up to 400 per $mm^3$.

The inventors speculate that the dense packing of primordial follicles within the cortical tissue may inhibit primordial follicle activation and subsequent growth. Therefore, in embodiments where primordial follicles are densely packed in the cortical tissue, the step of mechanically stretching the ovarian tissue sample may increase the separation between the primordial follicles within the cortical tissue. Such an increase in separation may reduce the concentration of inhibitory factors such as Anti-Müllerian hormone, for example, in the locality of the primordial follicles within the cortical tissue of the ovarian tissue sample, thereby reducing the inhibitory effect of a given primordial follicle on the neighbouring primordial follicles.

In any event, the step of mechanically stretching the ovarian tissue sample may have the effect of facilitating the activation of any primordial follicles that may be present within the cortical tissue of the ovarian tissue sample.

The ovarian tissue sample may be mechanically stretched along multiple dimensions of the ovarian tissue sample.

The step of mechanically stretching the ovarian tissue sample may increase the size of the ovarian tissue sample along the at least one dimension by at least 10%.

The greatest increase in the size of the ovarian tissue sample may be achieved when the ovarian tissue sample is mechanically stretched along the dimension of the ovarian tissue sample that is parallel to that of the longest connecting fibres of the ovarian tissue sample.

The ovarian tissue sample may relax back to approximately its original size after being mechanically stretched. The ovarian tissue sample may remain at the increased size, or substantially at the increased size, after the step of being mechanically stretched.

Preferably, the step of mechanically stretching the ovarian tissue sample does not result in tearing of the tissue and/or rupturing of cells and subsequent release of their contents.

The stromal tissue may form a layer over the cortical tissue. The thickness of the layer of stromal tissue may be greater than required, and therefore, the thickness of the layer of stromal tissue may be reduced by removing excess stromal tissue. The thickness of the layer of stromal tissue may be reduced to between 1 and 5 mm after the step of removal of excess stromal tissue from the ovarian tissue sample. The thickness of the layer of stromal tissue may be reduced to between 2 to 4 mm after the step of removal of excess stromal tissue from the ovarian tissue sample. Preferably, the thickness of the layer of stromal tissue is reduced to about 3 mm after the step of removal of excess stromal tissue from the ovarian tissue sample. Accordingly, "excess stromal tissue" is the stromal tissue that extends from the cortical tissue by more than between 1 and 5 mm, between 2 and 4 mm, or preferably about 3 mm.

The cortical tissue within the ovarian tissue sample may form a cortical surface on a first side of the ovarian tissue sample. The stromal tissue may form a stromal surface on a second side of the ovarian tissue, opposed to the first side.

The surface area of the cortical surface may be at least 1 to 2 times the surface area of the stromal surface after the step of mechanically stretching the ovarian tissue sample. The surface area of the cortical surface may be at least 1.3 to 1.7 times the surface area of the stromal surface after the step of mechanically stretching the ovarian tissue sample. Preferably, the surface area of the cortical surface is about 1.5 times the surface area of the stromal surface after the step of mechanically stretching the ovarian tissue sample. Accordingly, the ovarian tissue sample may have a ratio of cortical surface area to stromal surface area of between 1:1 to 2:1. Preferably, the ratio of cortical surface area to stromal surface area is 3:2.

After the step of mechanically stretching the ovarian tissue sample, the ovarian tissue sample may be cut into a plurality of smaller ovarian tissue fragments. The ovarian tissue sample may be cut at an angle such that the surface area of the cortical surface is greater than the surface area of the stromal surface. The ovarian tissue sample may be cut at an angle of between 30° and 60° to the plane of the cortical surface. Preferably, the ovarian tissue sample is cut at an angle of about 45° to the plane of the cortical surface.

In embodiments where the ovarian tissue sample is cut at opposing ends, the resulting tissue fragments may be trapezoidal prisms. In embodiments where the ovarian tissue sample is cut at two sets of opposing sides such that the resulting cortical surface is rectangular, the tissue fragments may be frusto-pyramidal. In this way, the invention may be a method of preparing ovarian tissue and/or ovarian tissue fragments for primordial follicle growth.

The cortical tissue may comprise a population of endogenous ovarian follicles, and growth of the endogenous ovarian follicles may be facilitated during the step of mechanically stretching the ovarian tissue sample.

By the term "endogenous ovarian follicles" we refer to those ovarian follicles that were originally within the ovarian tissue sample when the ovarian tissue sample was obtained.

Endogenous ovarian follicles within the population of endogenous ovarian follicles with a diameter greater than 80 µm may be mechanically removed from the ovarian tissue. Preferably, endogenous ovarian follicles within the population of endogenous ovarian follicles with a diameter greater than 100 µm are mechanically removed from the ovarian tissue. Endogenous ovarian follicles within the population of endogenous ovarian follicles with a diameter greater than 80 µm, or greater than 100 µm may be mechanically removed from the ovarian tissue after the step of mechanically stretching the ovarian tissue sample.

Endogenous ovarian follicles of about 80 µm or larger have been observed to have an inhibitory effect on the activation and subsequent growth of primordial follicles, and therefore, removal of these larger endogenous ovarian follicles minimises these inhibitory effects, thereby increasing the potential number of endogenous ovarian follicles whose growth is subsequently activated.

In one embodiment of the invention, a population of ovarian stem cells is introduced into the ovarian tissue sample after the step of mechanically stretching the ovarian tissue sample. The population of ovarian stem cells may be introduced into an ovarian tissue sample comprising endogenous ovarian follicles. The population of ovarian stem cells may be introduced into an ovarian tissue sample that does not comprise endogenous ovarian follicles.

Typically, the population of ovarian stem cells comprises between 100 and 10,000 ovarian stem cells.

A subset of the population of ovarian stem cells may differentiate into exogenous ovarian follicles within the cortical tissue. Preferably, a majority of the ovarian stem cells within the population of ovarian stem cells differentiate into exogenous ovarian follicles within the cortical tissue.

For example, an ovarian tissue sample may comprise between 1 and 100 exogenous ovarian follicles.

By the term "exogenous ovarian follicles" we refer to those ovarian follicles that were not originally present within the ovarian tissue sample when the ovarian tissue sample was obtained, and have since been added to the ovarian tissue sample. For example, ovarian stem cells that have been added to the ovarian tissue sample may differentiate into exogenous ovarian follicles.

In embodiments of the invention where the ovarian tissue sample comprises endogenous ovarian follicles and a population of ovarian stem cells are introduced into the ovarian tissue sample that differentiate into exogenous ovarian follicles, the exogenous ovarian follicles may grow alongside the endogenous ovarian follicles within the ovarian tissue sample. It may be that the exogenous ovarian follicles are labelled with a marker to allow the exogenous ovarian follicles to be differentiated from the endogenous ovarian follicles. The marker may be a fluorescent marker. The fluorescent marker may comprise a fluorescent protein such as green-fluorescent protein (GFP) or a GFP derivative, for example, or may comprise an alternative fluorophore moiety such as fluorescent Dextrans, for example. Accordingly, the exogenous ovarian follicles may be visually differentiated from the endogenous ovarian follicles when the ovarian tissue sample is illuminated with a wavelength of light that will induce fluorescence of the fluorescent marker.

Typically, the distribution and density of primordial endogenous ovarian follicles within the cortical tissue of a given ovarian tissue sample is not uniform and can vary greatly between ovarian tissue samples, typically between 0 and 400 follicles per $mm^3$, and may be related to several factors including species, age, hormone cyclicity and drug treatments/illness of the subject from which the ovarian tissue sample has been obtained.

Therefore, the cortical tissue of a given ovarian tissue sample may not comprise any endogenous ovarian follicles. Accordingly, in embodiments where a population of ovarian stem cells are introduced into the cortical tissue and that cortical tissue does not comprise primordial endogenous ovarian follicles, the method may be a method of preparing ovarian tissue for exogenous ovarian follicle growth.

Preferably, the ovarian tissue sample is cultured in a serum-free media comprising follicle stimulating hormone (FSH) for at least twenty four hours. The ovarian tissue sample may be cultured in a serum-free media comprising FSH for at least twenty four hours after the step of mechanically stretching the ovarian tissue sample. In embodiments where a population of ovarian stem cells are added to the ovarian tissue sample, the ovarian tissue sample may be cultured in a serum-free media comprising FSH for at least twenty four hours after the step of adding a population of ovarian stem cells to the ovarian tissue sample.

The serum-free media may comprise between 0.5 ng/ml to 2.5 ng/ml FSH. Preferably, the serum-free media comprises at least 1 ng/ml FSH. Preferably, the serum-free media comprises less than 2.5 ng/ml.

In embodiments where the ovarian tissue sample is a bovine ovarian tissue sample, bovine serum, activin-A, bpV(HOpic), 740-YP, GDF-9 or BMP15 individually or in combination may be contra-indicated in ovarian tissue culture. That is, preferably, the serum-free media does not comprise bovine serum, activin-A, bpV(HOpic), 740-YP, GDF-9 or BMP15.

In embodiments where the ovarian tissue sample is a human ovarian tissue sample, human serum, activin-A, bpV(HOpic), 740-YP, GDF-9 or BMP15 individually or in combination may be contra-indicated in ovarian tissue culture. That is, preferably, the serum-free media does not comprise human serum, activin-A, bpV(HOpic), 740-YP, GDF-9 or BMP15.

Furthermore, tissue viability may be adversely affected by alteration of the FSH concentration outside of the ranges described above. In addition, it is preferred that the serum-free media does not comprise antibiotic insulin combination products.

In embodiments where a population of ovarian stem cells are added to the ovarian tissue, it may be that subsequently culturing the ovarian tissue allows the ovarian stem cells within the cortical tissue of the ovarian tissue sample to differentiate into exogenous ovarian follicles. Typically, culturing the ovarian tissue sample for at least twenty four hours allows growth of the endogenous and/or exogenous ovarian follicles to be activated.

Preferably, a population of isolated ovarian somatic support cells are introduced into the cortical tissue of the ovarian tissue sample after culturing for at least twenty four hours. The population of isolated ovarian somatic support cells may be isolated ovarian stromal cells. The population of isolated ovarian somatic support cells may be predominantly ovarian stromal cells. The population of isolated ovarian somatic support cells may be introduced at a concentration of 2,000-4,000 cells per 5 µL. Suitably, 20,000-40,000 cells may be introduced into the cortical tissue.

Preferably, the population of isolated ovarian somatic support cells is introduced at a concentration of at least 2,000 cells per 5 µl.

By the term "isolated ovarian somatic support cells", we refer to ovarian somatic support cells that are the product of enzymatically processing ovarian tissue.

By the term "isolated ovarian stromal cells", we refer to ovarian stromal cells that are the product of enzymatically processing ovarian tissue.

The isolated ovarian somatic support cells may be a mixed population of stromal cell types. The stromal cell types within the isolated ovarian somatic support cells may comprise spindle shaped, ellipsoid and circular cells, for example. The isolated ovarian somatic support cells may be typically between 1 and 15 µm in diameter, preferably between 5 and 10 µm in diameter. The isolated ovarian somatic support cells may comprise or express markers. The isolated ovarian somatic support cells may be identified by the markers that they comprise or express. The isolated ovarian somatic support cells may comprise or express a plurality of markers. The plurality of markers may comprise FoxL2, CoupTFII and bFGF, for example. Alternatively, the isolated somatic support cells may lack or not express one or more markers. The one or more markers may comprise DDX4, for example, and the isolated somatic support cells may therefore be DDX4 negative.

Applicants have found that the introduction of the isolated ovarian somatic support cells into the cortical tissue once the growth of the ovarian follicles present within the cortical tissue has been activated results in a greater number of viable and healthy follicles that may subsequently be extracted from the cortical tissue to form oocytes.

Without wishing to be bound be theory, the introduction of ovarian somatic support cells after the endogenous and/or exogenous ovarian follicles have been activated may have the effect of enriching the ovarian tissue sample, providing an improved environment within which the activated ovarian follicles can grow, and results in an improvement in the health of the growing ovarian follicles, and an increase in the number of growing ovarian follicles that may be isolated.

After the step of introducing a population of isolated ovarian somatic support cells into the cortical tissue, the ovarian tissue sample may then be cultured for a further period of at least four days. Preferably, the further period is at least five days, and more preferably at least six days. Preferably, the further period is between four and eight days. Typically, by the end of the further period growing follicles can be observed on the ovarian tissue surface.

Typically, whilst the ovarian tissue sample is cultured for a further period, the ovarian follicles within the cortical tissue of the ovarian tissue sample grow.

The invention extends in a second aspect to a method of preparing individual ovarian follicles comprising the steps:
- providing an ovarian tissue sample prepared via the method of the first aspect of the invention;
- selecting and mechanically extracting from the ovarian tissue sample individual ovarian follicles; and
- placing each individual extracted ovarian follicle in separate culture media.

The individual ovarian follicles mechanically extracted from the ovarian tissue sample may be of at least 70 µm in diameter, and preferably of at least 80 µm in diameter.

There is evidence that growth of ovarian follicles is inhibited by the presence of additional ovarian follicles once the ovarian follicles have grown beyond a defined stage. For example, growth of ovarian follicles may be inhibited by the presence of additional ovarian follicles once the ovarian follicles have a diameter of at least 70 µm, 80 µm, or 100 µm.

Therefore, the step of extracting and separating the ovarian follicles from the ovarian cortical tissue may have the effect of encouraging the growth of each separated ovarian follicle, and thereby increases the final number of viable and healthy ovarian follicles from which healthy oocytes may be extracted.

Accordingly, the method of the present aspect of the invention may result in a higher population of viable, growing ovarian follicles from a given number of primordial ovarian follicles than other methods known in the art.

Extracting individual ovarian follicles from the ovarian tissue sample using non-mechanical means, such as by the use of enzymes, has been observed by the inventors to have a negative impact on the viability of the individual ovarian follicles and resulting oocytes. Therefore, mechanically extracting individual follicles from the ovarian tissue sample improves the viability of the individual ovarian follicles and resulting oocytes than using non-mechanical means, such as enzymes.

Each individual extracted ovarian follicle may be placed in separate culture media in separate vessels. For example, the vessels may be wells within a plate and one extracted ovarian follicle may occupy one well within the plate.

The culture media into which the separated extracted ovarian follicles are placed may comprise follicle stimulating hormone (FSH). The culture media may comprise at least 0.5 ng/ml FSH, or at least 1.0 ng/ml FSH. The culture media may comprise activin-A. The culture media may comprise at least 50 ng/ml activin-A, or at least 100 ng/ml activin-A.

The extracted ovarian follicles may be cultured in the culture media for a culturing period. The concentration of FSH may be varied during the culturing period. The concentration of FSH may be increased during the culturing period. For example, the concentration of FSH may be 1 ng/ml FSH for the first 48 hours increasing to 10 ng/ml for a further 96 hours.

Typically, the ovarian follicles that are extracted from the ovarian tissue sample include any ovarian follicle that is at least 70 µm in diameter. Therefore, in embodiments where the ovarian tissue sample comprises endogenous ovarian follicles and/or exogenous ovarian follicles, an extracted ovarian follicle may be an endogenous ovarian follicle or an exogenous ovarian follicle.

According to a third aspect of the invention, there is provided a method of preparing individual ovarian follicles for growth comprising the steps:
- providing an ovarian tissue sample comprising cortical tissue and stromal tissue;
- removing damaged tissue from the ovarian tissue sample where present;
- removing excess stromal tissue from the ovarian tissue sample where present;
- mechanically stretching the ovarian tissue sample along at least one dimension of the ovarian tissue sample, such that the size of the ovarian tissue sample along the at least one dimension is increased by at least 10%;
- culturing the ovarian tissue sample in a serum-free medium comprising Follicle Stimulating Hormone (FSH) for at least twenty four hours;
- adding a population of isolated ovarian somatic support cells into the ovarian tissue sample;
- culturing the ovarian tissue sample for a further period of at least four days; and
- mechanically removing individual growing follicles from the ovarian tissue sample.

Preferably, the cortical tissue comprises a population of endogenous ovarian follicles and individual growing follicles from the population of endogenous ovarian follicles are mechanically removed from the cortical tissue.

Accordingly, the method may be a method of preparing individual endogenous ovarian follicles that may be grown into viable and healthy oocytes.

The method may comprise the step of introducing a population of ovarian stem cells into the cortical tissue between the steps of mechanically stretching the ovarian tissue sample and culturing the ovarian tissue sample for at least twenty four hours, such that at least a subset of the population of ovarian stem cells differentiate into a population of exogenous ovarian follicles within the cortical tissue. Therefore, in embodiments where the cortical tissue comprises a population of endogenous ovarian follicles, the method may be a method of preparing individual exogenous ovarian follicles and endogenous ovarian follicles.

Typically, the distribution of endogenous ovarian follicles within the cortical tissue of a given ovarian tissue sample is not uniform and can vary greatly between ovarian tissue samples. Therefore, the cortical tissue of a given ovarian tissue sample may not comprise any endogenous ovarian follicles. Accordingly, in embodiments where a population of ovarian stem cells are introduced into the cortical tissue and that cortical tissue does not comprise endogenous ovarian follicles, the method may be a method of preparing individual exogenous ovarian follicles only.

After the step of mechanically stretching the ovarian tissue sample, and before the step of culturing the ovarian tissue sample for at least twenty four hours, the ovarian tissue sample may be cut into a plurality of ovarian tissue fragments. The ovarian tissue sample may be cut at an angle such that the surface area of the cortical surface is greater than the surface area of the stromal surface. The ovarian tissue sample may be cut at an angle of between 30° and 60° to the plane of the cortical surface. Preferably, the ovarian tissue sample is cut at an angle of about 45° to the plane of the cortical surface.

The surface area of the cortical surface may be at least 1 to 2 times the surface area of the stromal surface after the step of mechanically stretching the ovarian tissue sample. The surface area of the cortical surface may be at least 1.3 to 1.7 times the surface area of the stromal surface after the step of mechanically stretching the ovarian tissue sample. Preferably, the surface area of the cortical surface is about 1.5 times the surface area of the stromal surface after the step of mechanically stretching the ovarian tissue sample. Accordingly, the ovarian tissue sample may have a ratio of cortical surface area to stromal surface area of between 1:1 to 2:1. Preferably, the ratio of cortical surface area to stromal surface area is 3:2.

In embodiments where the ovarian tissue sample is cut at opposing ends, the resulting tissue fragments may be trapezoidal prisms. In embodiments where the ovarian tissue sample is cut at two sets of opposing sides such that the resulting cortical surface is rectangular, the tissue fragments may be frusto-pyramidal. In this way, the ovarian tissue that is cultured after the step of mechanically stretching the ovarian tissue sample may be an ovarian tissue fragment or the original ovarian tissue sample.

The mechanically removed individual growing follicles may each be grown further separately. For example, each growing follicle may be placed in a separate well containing appropriate culture media after it has been mechanically removed from the ovarian tissue.

Typically, individual growing follicles have reached a diameter of about 70 μm to 100 μm after the step culturing the ovarian tissue sample for at least a further four days, at which point they may begin to have an inhibitory effect on the growth of neighbouring follicles. Therefore, it is important that the growing follicles are separated and each cultured individually to minimise any inhibition.

The further period for culturing the ovarian tissue sample may be of at least five days or at least six days. Typically, the ovarian tissue sample is cultured for a further period until growing follicles can be observed on the ovarian tissue surface.

Preferred and optional features of the first and second aspects are preferred and optional features of the third aspect.

According to a fourth aspect of the invention, there is provided a method of releasing an oocyte-cumulus complex from an ovarian follicle, comprising the steps:
  providing an ovarian follicle within a medium, the ovarian follicle comprising an oocyte-cumulus complex and a basal laminar;
  mechanically breaching the basal laminar of the ovarian follicle; and
  releasing the oocyte-cumulus complex from the ovarian follicle.

Preferably, the ovarian follicle is provided by the method of the second aspect of the invention, or by the third aspect of the invention.

The ovarian follicle may be an antral ovarian follicle. That is, the ovarian follicle may have matured sufficiently to comprise an antral cavity and the oocyte-cumulus complex may be within the antral cavity. The ovarian follicle may be a pre-antral ovarian follicle. That is, the ovarian follicle may not have matured sufficiently to comprise an antral cavity.

Typically, the ovarian follicle has a diameter of at least 150 μm. Preferably, the ovarian follicle has a diameter of at least 200 μm.

Applicant has found that the step of breaching the basal laminar of the ovarian follicle must be carried out mechanically to ensure that the oocyte-cumulus complex is not damaged during the process of being released from the ovarian follicle. For example, breaching the basal laminar of the ovarian follicle using enzymes may lead to degradation of the oocyte-cumulus complex, or destruction of the oocyte-cumulus complex.

Once the oocyte-cumulus complex has been released from the ovarian follicle, the oocyte-cumulus complex may be transferred to a holding membrane, such that the oocyte cumulus complex is supported on the holding membrane.

Multiple oocyte-cumulus complexes may be retained on a single holding membrane. For example, a single holding membrane may retain and support up to 6 oocyte/cumulus complexes.

In embodiments where the holding membrane retains and supports multiple oocyte-cumulus complexes, each oocyte-cumulus complex retained on a single holding membrane are preferably of a similar diameter. Accordingly, each oocyte-cumulus complex on the holding membrane will be at a similar stage of growth and have similar nutritional requirements, and therefore, these requirements can be readily met for each complex on the membrane at the same time.

The holding membrane may comprise pores of between 1 and 20 μm in diameter. The holding membrane may comprise pores of between 5 and 15 μm in diameter. Preferably, the holding membrane comprises pores of between 5 and 10 μm in diameter. Accordingly, the holding membrane may allow the passage of nutrients from the culture medium to the oocyte-cumulus complex retained on the holding membrane. For example, the holding membrane may be a track-etched nucleopore membrane, or a nitrocellulose membrane with pores of approximately 8 μm in diameter. The holding membrane may maintain the physical contact between the oocyte within the oocyte-cumulus complex and the surrounding cells. The holding membrane may maintain the correct complex architecture to allow the oocyte within the complex to grow.

The oocyte-cumulus complex on the holding membrane may be cultured in culture medium. The oocyte-cumulus complex on the holding membrane may be cultured in culture medium until the oocyte within the oocyte-cumulus complex grows to a diameter of at least 100 μm. The oocyte within the oocyte-cumulus complex on the holding membrane may be cultured in culture medium. The culture medium may be covered until a first polar body is expelled from the oocyte to seal the culture medium from air, and to prevent evaporation or dilution of the culture medium. The culture medium may be covered with a liquid that is immiscible with the culture medium. Preferably, the culture medium may be covered with mineral oil until a first polar body is expelled from the oocyte.

The invention therefore, extends in a fifth aspect to a method of growing viable oocyte in vitro, comprising the steps:
  providing an ovarian tissue sample comprising cortical tissue and stromal tissue, the cortical tissue comprising a population of endogenous ovarian follicles;
  removing damaged tissue from the ovarian tissue sample where present;
  removing excess stromal tissue from the ovarian tissue sample where present;
  mechanically stretching the ovarian tissue sample along at least one dimension of the ovarian tissue sample, such that the size of the ovarian tissue sample along the at least one dimension is increased by at least 10%;
  culturing the ovarian tissue sample in a serum-free media comprising Follicle Stimulating Hormone (FSH) for at least twenty four hours;
  adding a population of isolated ovarian somatic support cells into the ovarian tissue sample;
  culturing the ovarian tissue sample for at least a further four days;
  mechanically extracting individual growing follicles of at least 80 μm in diameter from the population of endogenous growing follicles in the ovarian tissue sample;
  placing each individual extracted ovarian follicle in culture media comprising FSH and activin A and culturing the individual ovarian follicles for at least 6 days, such that the individual ovarian follicles comprise an oocyte-cumulus complex, and a basal laminar;

mechanically breaching the basal laminar of the ovarian follicle to thereby release the oocyte-cumulus complex from the ovarian follicle;

transfer the oocyte-cumulus complex to a holding membrane, such that the oocyte cumulus complex is supported on the holding membrane;

culture the oocyte-cumulus complex on the holding membrane in culture medium until the oocyte within the oocyte-cumulus complex grows to a diameter of at least 100 µm; and culture the oocyte on the holding membrane in culture medium and sealing the culture medium from air until a first polar body is expelled from the oocyte.

The method may comprise the step of introducing a population of ovarian stem cells into the cortical tissue such that at least a subset of the population of ovarian stem cells differentiate into a population of exogenous ovarian follicles after the step of stretching the ovarian tissue sample. Accordingly, the method may be a method of growing viable oocyte in vitro from endogenous ovarian follicles and exogenous ovarian follicles.

The individual ovarian follicles may be cultured until they comprise an antral cavity.

The individual extracted ovarian follicles may be cultured in media comprising between 0.5 ng/ml to 2.5 ng/ml FSH, preferably comprising 1 ng/ml FSH.

Typically, the culture medium containing the oocyte on the holding membrane is covered to seal the culture medium from air, and to prevent evaporation or dilution of the culture medium until a first polar body is expelled from the oocyte. The culture medium may be covered with a liquid that is immiscible with the culture medium. Preferably, the liquid is an oil, such as mineral oil, or filtered mineral oil.

The invention may extend to a sixth aspect which relates to a method of growing viable oocyte in vitro comprising the steps of the fifth aspect of the invention, wherein the cortical tissue of the ovarian tissue sample does not comprise a population of endogenous ovarian follicles, and the method comprises the step of introducing a population of ovarian stem cells into the cortical tissue of the ovarian tissue sample after the step of mechanically stretching the ovarian tissue sample and before the step of culturing the ovarian tissue sample for at least twenty four hours, such that at least a subset of the population of stems cells differentiate into a population of exogenous ovarian follicles after the step of stretching the ovarian tissue sample.

Accordingly, the method may be a method of growing viable oocytes in vitro from exogenous ovarian follicles derived from ovarian stem cells.

According to a seventh aspect of the invention, there is provided a population of isolated ovarian somatic support cells for use in the method of preparing ovarian tissue samples according to any one of the first to sixth aspects of the invention, wherein the population of isolated ovarian somatic support cells form sheet-like structures when cultured alone in vitro.

The population of isolated ovarian somatic support cells may be a mixed population of ovarian stromal cell types. The ovarian stromal cell types within the isolated ovarian somatic support cells may comprise spindle shaped, ellipsoid and circular cells, for example. The isolated ovarian somatic support cells may be typically between 5 and 10 µm in diameter. The isolated ovarian somatic support cells may comprise or express marker proteins. The isolated ovarian somatic support cells may be identified by the marker proteins that they comprise or express. The isolated ovarian somatic support cells may comprise or express a plurality of marker proteins. The plurality of marker proteins may comprise FoxL2, CoupTFII and bFGF, for example. Alternatively, the isolated somatic support cells may lack or not express one or more markers. The one or more markers may comprise DDX4, for example, and the isolated somatic support cells may therefore be DDX4 negative.

It is speculated that the introduction of a population of isolated ovarian somatic support cells into the cortical tissue of an ovarian tissue sample may provide an enriched environment for follicle development. Activated follicles may migrate to areas of the cortical tissue enriched by the population of ovarian stromal cells. It would appear that physical contact between the stromal cells and the activated follicles promotes growth of the activated follicle.

Typically, the population of isolated ovarian somatic support cells are suspended in a suitable medium. The suitable medium may comprise OSC medium (MEMα GlutaMAX supplemented with 10% FBS, 10 µl/ml N2 supplement, 10 µl/ml 100× pen-strep-glutamine, 1 mM nonessential amino acids, 1 mM sodium pyruvate, 100 units/ml leukaemia inhibitory factor, 10 ng/ml recombinant human epidermal growth factor, 1 ng/ml basic fibroblast growth factor, 40 ng/ml glial cell-derived neurotropic factor).

It may be that the population of isolated ovarian somatic support cells are provided as a pellet and it is necessary to re-suspend them in suitable media before being used in the method of any one of the preceding aspects of the invention.

The isolated ovarian somatic support cells may be derived from processing ovarian stromal tissue. The isolated ovarian somatic support cells may be derived from stromal tissue removed from ovarian tissue samples to be used in the methods of the first to sixth aspects of the invention. Alternatively, or in addition, the isolated ovarian somatic support cells may be derived from processing ovarian stromal tissue removed for other purposes.

In an eighth aspect of the invention, there is provided culture medium for use in the methods of culturing ovarian tissue according to the first aspect, wherein the culture medium is serum-free and comprises between 0.5 ng/ml and 2.5 ng/ml of follicle stimulating hormone (FSH).

Preferably, the medium comprises 1 ng/ml of FSH.

For example, in embodiments where the ovarian tissue sample is a bovine ovarian tissue sample, the culture medium may be McCoys 5A HEPES modified medium with bovine serum albumin (0.1% by weight), L-glutamine (3 mM), benzyl penicillin (1 mg/ml), streptomycin sulphate (1 mg/ml), bovine transferrin (2.5 µg/ml), selenium (4 ng/ml), bovine insulin (10 ng/ml), FSH (1 ng/ml) & ascorbic acid (50 µg/ml).

In an alternative example, in embodiments where the ovarian tissue sample is a human ovarian tissue sample, the culture medium may be McCoys 5A HEPES modified medium with human serum albumin (0.1% by weight), L-glutamine (3 mM), benzyl penicillin (1 mg/ml), streptomycin sulphate (1 mg/ml), human transferrin (2.5 µg/ml), selenium (4 ng/ml), human insulin (10 ng/ml), FSH (1 ng/ml) & ascorbic acid (50 µg/ml).

According to a ninth aspect of the invention, there is provided culture medium for use in the method of growing isolated ovarian follicles of the fourth, fifth or sixth aspect of the invention, wherein the culture medium comprises between 0.5 and 1.5 ng/ml FSH.

Preferably, the culture medium comprises 1 ng/ml FSH.

The culture medium may comprise between 50 and 150 ng/ml activin-A. Preferably, the culture medium comprises between 75 and 125 ng/ml activin-A. More preferably, the culture medium comprises 100 ng/ml activin-A.

The FSH concentration may be adjusted as isolated ovarian follicle culture progresses. The FSH concentration may be increased as the isolated ovarian follicle culture progresses. For example, the culture medium may comprise 1 ng/ml FSH for the first 48 hours increasing to 10 ng/ml for at least a further 96 hours further increasing to 100 ng/ml if the isolated ovarian follicles are cultured for 8 days or more.

For example, in embodiments where the ovarian tissue sample is a human ovarian tissue sample, the initial culture medium may be McCoy's 5A HEPES modified medium with human serum albumin (0.1% by weight), L-glutamine (3 mM), benzyl penicillin (1 mg/ml), streptomycin sulphate (1 mg/ml), human transferrin (2.5 µg/ml), selenium (4 ng/ml), human insulin (10 ng/ml), FSH (1 ng/ml), ascorbic acid (50 µg/ml), Kit Ligand (10 µg/ml) & recombinant activin A (100 ng/ml), and the concentration of FSH is increased to 10 ng/ml after the first 48 hours of culture, and further increased to 100 ng/ml after 8 days of culture.

Estradiol may be added to the culture medium after an initial period of culture.

For example, between 50 and 150 ng/ml estradiol may be added to the culture after an initial period of culture.

Additional estradiol may be added to the culture medium after a further period of culture. For example, the concentration of estradiol may be increased to 1 µg/ml after a further period of culture.

The initial period of culture may be 48 hours, and the further period may be six days, or eight days. For example, in one embodiment, 100 ng/ml estradiol is added to the culture medium after an initial period of 48 hours of culture at the same time that the concentration of FSH is increased from 1 ng/ml to 10 ng/ml. After a further period of eight days, if follicles remained in culture, the concentration of estradiol was increased to 1 µg/ml at the same time that the concentration of FSH was increased to 100 ng/ml.

In a tenth aspect of the invention, there is provided culture medium for use in the method of growing oocytes of the fourth, fifth or sixth aspect of the invention, wherein the culture medium comprises between 50 and 150 ng/ml FSH.

The culture medium may comprise sodium pyruvate. The culture medium may comprise kanamycin sulphate. The culture medium may comprise transferrin. The culture medium may comprise insulin-like growth factor 1 (IGF-1). The culture medium may comprise estradiol. The culture medium may comprise epidermal growth factor (EGF).

Preferably, the culture medium comprises FSH, sodium pyruvate, kanamycin sulphate, transferrin, IGF-1, EGF and estradiol.

For example, the culture medium may be McCoys 5A HEPES modified medium with bovine serum albumin (0.1% by weight), sodium pyruvate (2 mM), L-glutamine (3 mM), kanamycin sulphate (0.08 mg/ml), bovine transferrin (2.5 µg/ml), selenium (4 ng/ml), bovine insulin (10 ng/ml), FSH (100 ng/ml), IGF-1 (200 ng/ml), estradiol (1 µg/ml) & EGF (100 ng/ml).

Embodiments of the present invention will now be described, by way of non-limiting example, with reference to the accompanying drawings.

SPECIFIC DESCRIPTION OF EMBODIMENTS OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
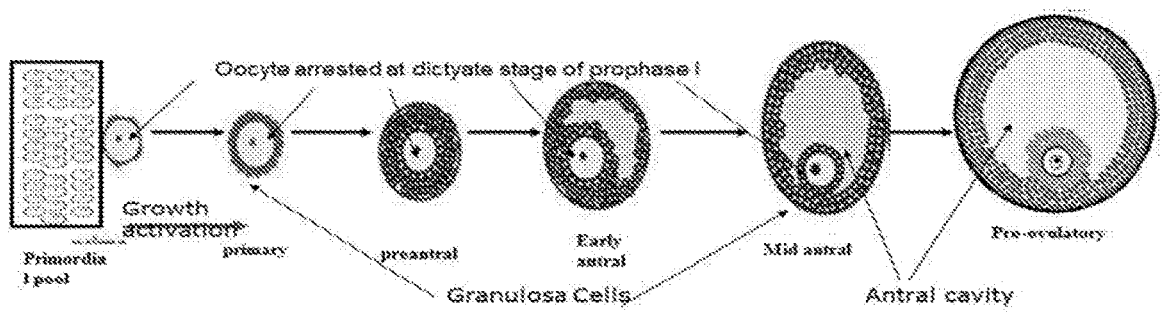
FIG. 1 shows the stages of follicle/oocyte development in vivo, where a pool of "resting" primordial follicles are gradually activated to grow throughout life. In humans and cows i.e. mono-ovulatory species, only one pre-ovulatory follicle will be formed during any reproductive cycle (i.e. 1 every 28 days in humans).
Figure 2:
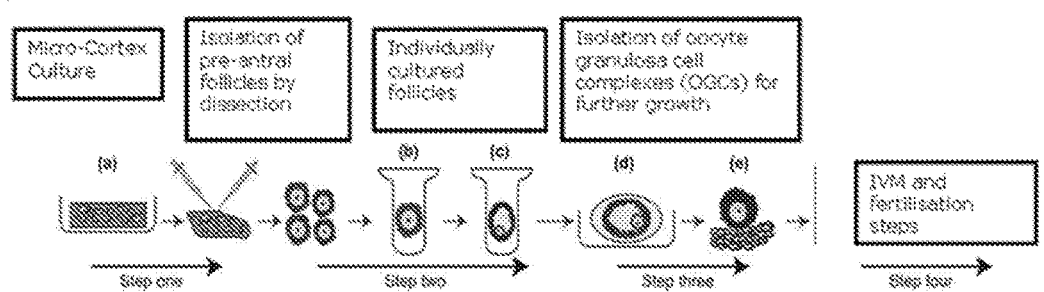
FIG. 2 A. Representation of the 4 steps required to support in vitro oocyte development as described by this invention. Flattened strips of ovarian tissue (a) are cultured free floating in medium. Once follicles have reached multi-laminar stages they are isolated mechanically using needles and then cultured individually (b). Isolated follicle culture supports development from pre-antral to antral stages (c). The final stages of oocyte growth and development are achieved by removing the oocyte-cumulus complex from the antral follicle (d) and culturing the oocyte and its surrounding somatic cells (e). B. An in vitro grown antral follicle highlighting the complex that can be removed after first two steps of culture. C. Photomicrograph of a human in vitro grown (IVG) oocyte-cumulus cell complex isolated on a membrane for further growth (step 3), then placed in maturation medium for 24 hours. D. An IVG complex after maturation and formation of a polar body, indicative of progression to metaphase II; this is confirmed in E, where the metaphase II spindle of the oocyte (top) and polar body are immunostained.
Figure 2:
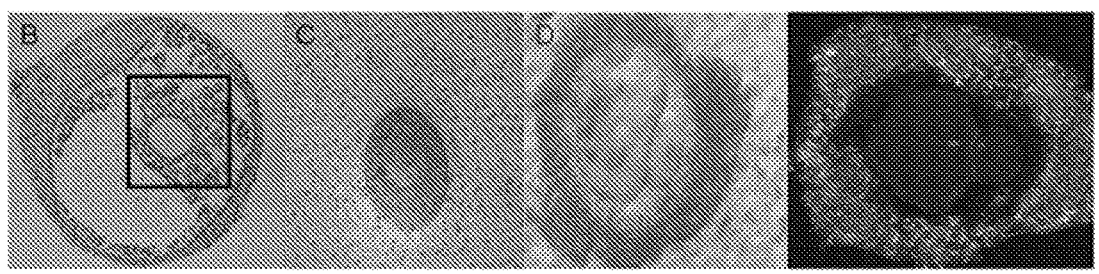
Figure 3:
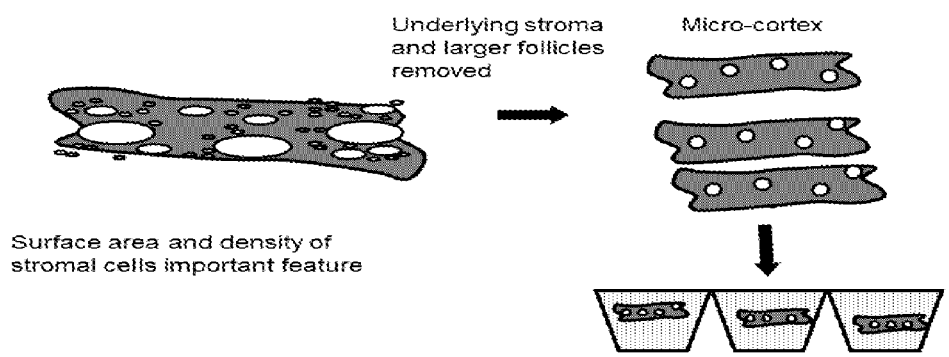
FIG. 3 illustrates the step of preparing the ovarian tissue sample to produce the so-called "micro-cortex"
Figure 4:
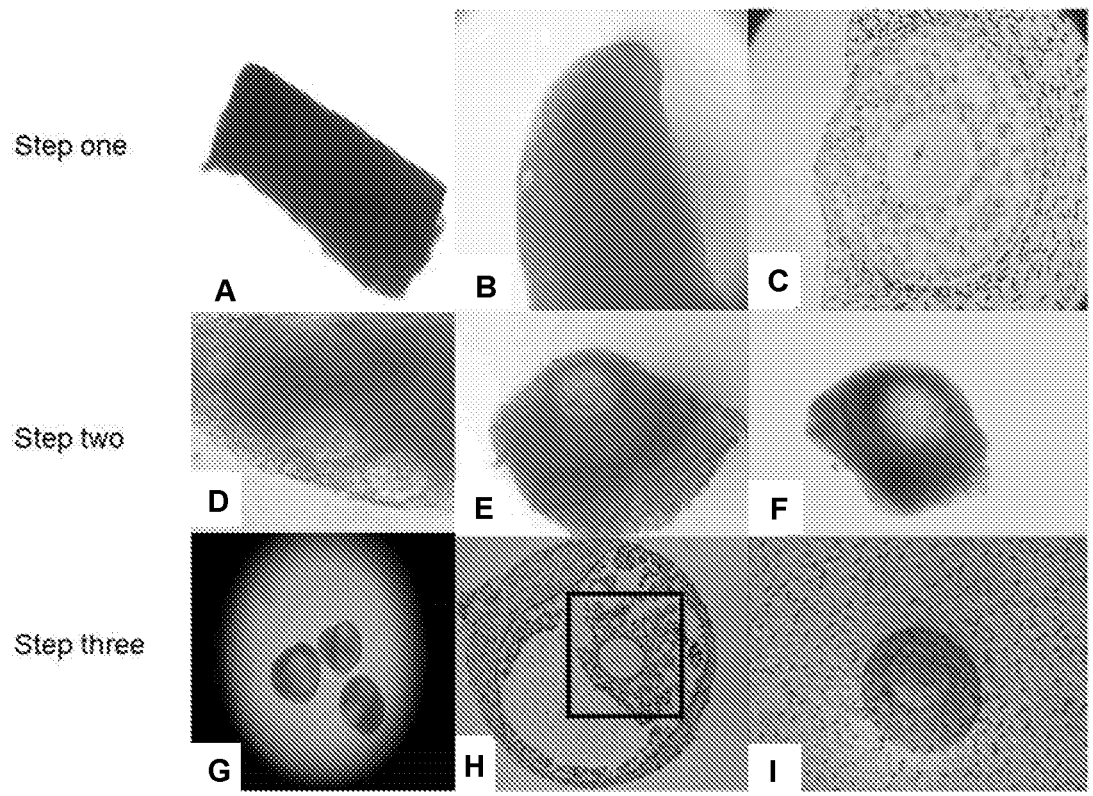
FIG. 4: Photomicrographs of each stage of the culture system showing a) micro-cortex at start of culture b) micro-cortex after 7 days in culture c) histological section of an in vitro grown follicle at end of stage 1 showing healthy oocyte and surrounding granulosa cells d) micro-cortex after step 1 showing growing follicles at the edge and ready for dissection e) Isolated growing follicle taken from micro-cortex with surrounding theca cells f) Isolated follicle grown in v well dish showing antral cavity formation g) antral follicles at end of stage 2 in preparation for removal of oocyte-cumulus complexes h) In vitro grown antral follicle with box defining oocyte-cumulus complex that will be removed for further growth i) oocyte-cumulus complex placed on membranes for final culture stage before in vitro maturation.
Figure 5:
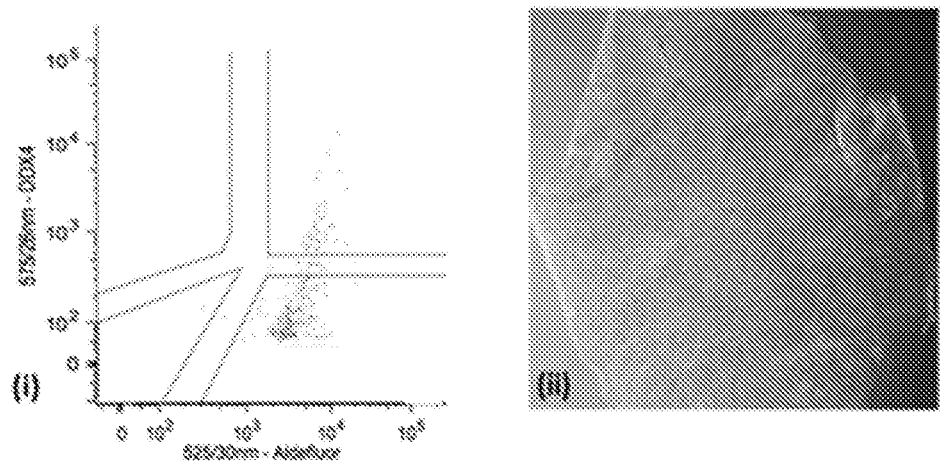
FIG. 5: (i). Adult human ovarian somatic support cells labelled with DDX4 and loaded with 303 ALDEFLUOR™. Human ovarian cells show a single emission profile of ALDEFLOUR™ (em.530/30 nm) (88.5% of the total sample). (ii) Single cell suspensions of ovarian somatic support cells form sheets when grown in vitro; and these can be harvested to supplement the ovarian cortex.
Figure 6:
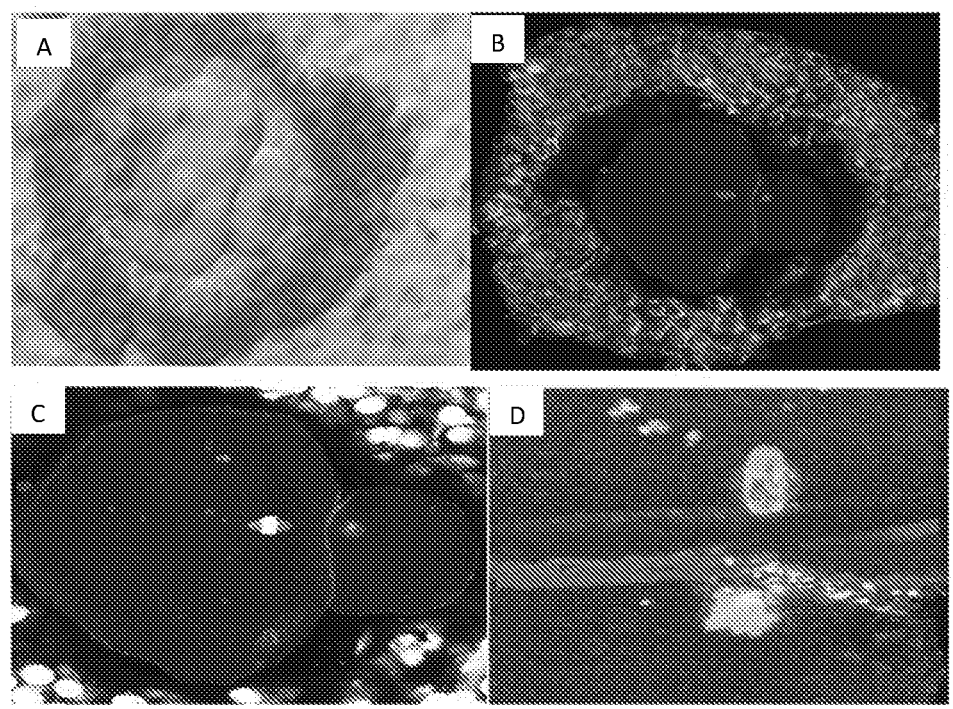
FIG. 6 a-d: a) Isolated Oocyte-Cumulus Complex taken from an in vitro grown follicle from human tissue and placed in maturation medium for final stage of development. A polar body has been formed (a,b) showing that these oocytes can resume meiosis a form a metaphase II spindle (c,d,).

With reference to the FIGS. 1 to 6, an example embodiment of the invention is described below.

Method for Tissue Preparation

Ovarian tissue samples were obtained by biopsy from human subjects and typically comprise cortical tissue with an exposed cortical surface on one side of the ovarian tissue, and medullary (or stromal) tissue with an exposed medullary (or stromal) surface on the opposed side of the ovarian tissue. The ovarian tissue samples typically have an uneven or puckered surface. The ovarian tissue was examined under light microscopy in a glass petri dish in holding medium (Leibovitz (L-15) medium with human serum albumin (0.3% by weight), sodium pyruvate (2 mM), L-glutamine (2 mM), benzyl penicillin (75 µg/ml), streptomycin sulphate (50 µg/ml)) at 37° C. to allow the surface of the cortical tissue to be distinguished from the underlying stromal tissue to minimize tissue damage and loss of ovarian follicles. Any follicles with a diameter larger than 100 µm were removed using 25 gauge needles to prevent the presence of these large developing follicles impeding the activation and growth of other follicles in the cortical tissue. Large follicles that were inaccessible or the tissue was particularly fibrous were removed using a no. 10 scalpel blade and fine forceps to prevent the tissue tearing.

Any torn, damaged or haemorrhagic areas of tissue were removed from the ovarian tissue using the tip of a no. 10 scalpel blade. With the surface of the medullary tissue uppermost the tissue was held using fine forceps, and excess medullary tissue was removed using a no. 24 scalpel blade to leave a 3 mm thick layer of medullary tissue above the cortical surface.

Preparation of Stretched Loosened Ovarian Tissue ("Micro-Cortex")

The ovarian tissue was then turned over to expose the cortical surface uppermost which should now be flattened. The tissue was then firmly anchored to the base of the petri dish using fine forceps to hold a small edge or corner of the tissue piece.

The blunt edge of a no. 10 scalpel blade was angled at 45° to the cortical surface and using gentle pressure drawn along the tissue surface stretching the tissue away from the anchor point. This may be repeated several times taking care not to rupture the tissue surface. With the cortical surface still uppermost the tissue was then cut into fragments (the "micro-cortex") approximately 0.5 mm long with a no. 24 scalpel blade using an incision angled at 45° to the cortical surface to ensure that each resulting fragment has a larger cortical surface area relative to the underlying tissue.

Individual tissue fragments were then transferred into separate wells within 24-well culture plates containing 300 µL of culture medium per well. Fine-bore sterile pastettes were used to transfer the tissue fragments to avoid tissue damage.

Day One of Culture:

Micro-cortex were suspended in medium (McCoys 5A HEPES modified medium with human serum albumin (0.1% by weight), L-glutamine (3 mM), benzyl penicillin (1 mg/ml), streptomycin sulphate (1 mg/ml), human transferrin (2.5 µg/ml), selenium (4 ng/ml), human insulin (10 ng/ml), recombinant human Follicle Stimulating Hormone (rhFSH) (1 ng/ml) & ascorbic acid (50 µg/ml)) and cultured for twenty four hours. Activation of follicles can be observed in the surface. After this initial twenty four hour culture, isolated ovarian somatic support cells (method of preparation of which described below) was added into the micro-cortex at a concentration of 2,000-4,000 cells per 5 µL delivered into 0.25 mm$^3$ of micro-cortex.

Surprisingly, the inventors have found that adding isolated ovarian somatic support cells back into the micro-cortex ovarian tissue fragments results in a significant improvement in the health of growing follicles and in an increase in the number of growing follicles that can be isolated to yield viable oocytes. The isolated ovarian somatic support cells may produce areas of dense stromal cells for growing follicles to move into to thereby provide a nurturing environment for the growth of healthy follicles and so increase the final yield of oocytes. The presence of additional stromal cells and 1 ng/ml rhFSH while the follicles grow within the micro-cortex ovarian tissue fragments increases the yield of growing follicles by 40-55%.

Preparation of Enriched Ovarian Somatic Support Cell Suspension:

This cell suspension is prepared by dissociation of pieces of ovarian cortex after removal of growing follicles. Tissue slices (of 0.2 mm$^3$) are prepared using a scalpel and needles (size and gauge) and are held in Leibovitz medium containing BSA (bovine isolation) or HSA (human isolation). To prepare for dissociation into a single cell suspension, tissue pieces are removed from the media and placed in a shallow petri dish. The tissue is reduced to a very small sections using the tip of fine scissors, transferred in HBSS supplemented with Mg and Ca with 1.2 U/ml collagenase I/II. Tissue is mechanically dissociated using a Gentlemacs Dissociator set on programs h_tumour 1, h_tumour 2 and h_tumour_3 running consecutively. Dissociated tissue is passed through a series of cell filters of decreasing pore size (100-30 µm) and enzymatic activity stopped by addition of a 2% NGS solution. The cell solution is transferred into a shallow glass petri dish and inspected under a light microscope to ensure no follicles or oocytes are present—any present are removed using a sterile fine pastette. Cells are now prepared for fluorescently activated cell sorting (FACS) by centrifuging the cell suspension at 300 g for 5 mins in HBSS minus Mg and Ca with 2% HSA and NGS (blocking solution). Supernatant is removed and the cell pellet re-suspended in 1 ml of blocking solution. Aliquots are taken for secondary only and control samples and the remaining cell suspension re-pelleted (300 g for 5 mins). Supernatant is removed and the cell pellet is labelled with anti-rabbit DDX4 antibody (abcam 13840, 1 in 10) and incubated on ice for one hour. Following incubation cells are re-pelleted (300 g for 5 mins) twice then labelled with a secondary antibody (donkey anti-rabbit IgG conjugated to cyanine 3, 1 in 300) and incubated for 30 mins on ice. Following secondary antibody incubation cells are pelleted (300 g for 5 mins) and washed twice before being labelled with Aldefluor™ reagent for 30 mins at 37° C. Cells are pelleted (300 g for 5 mins) and washed once following Aldefluor™ incubation, re-suspended in 500 µl of blocking solution and subjected to FACS. Cells positive for Aldefluor™ and negative for the germline marker DDX4 are collected and re-suspended in medium.

The cell suspension is loaded into large blastomere needles and 20 µl micro-injected into two or three locations of the micro cortex preparation. These cells when cultured by themselves form characteristic sheet like structures in vitro (for example, see FIG. 5).

TABLE 1

Summary of morphological and molecular characteristics of ovarian somatic support cells (OSSCs) utilised to enrich the ovarian environment improving follicle survival and development. OSSCs collected from ovarian single cell suspension labelled with DDX4 antibody and Aldefluor™ and subjected to FACS.

| Morphology | Location | Size | FACS | cDNA expression | Immunoblot |
|---|---|---|---|---|---|
| Ovarian stromal cell i.e. spindle, ellipsoid or spherical | Medulla and cortico-medullary interface | Mean diameter 3-6 µm | Aldefluor positive; DDX4 negative | POU5F1 Lin28 | Foxl2 Coup-TFII bFGF |

Characterisation of the Enriched Ovarian Stromal Cell Suspension

The population of isolated ovarian somatic support cells within the enriched ovarian stromal cell suspension were observed to comprise spindle shaped, ellipsoid and circular cells and these cells were between 5 and 10 µm in diameter. The isolated ovarian somatic support cells were characterised by being negative for DDX4.

Isolation of Growing Follicles

After 6-8 days of micro-cortex culture follicles with a diameter of at least 80 µm were observed that were ready to be removed for further growth. These follicles were removed mechanically from the tissue by dissection with 25 gauge needles. The use of enzymes at this stage compromises oocyte/follicle viability, and therefore, enzymes are not used. After dissection only those follicles with an intact basal membrane and surrounding theca cells were selected for culture. Mechanically isolated growing follicles are placed individually into 96-well V-bottomed culture plates (Corning Costar Europe, Badhoevedorp, The Netherlands) in 150 µL of supplemented McCoy's culture medium (McCoy's 5A HEPES modified medium with human serum albumin (0.1% by weight), L-glutamine (3 mM), benzyl penicillin (1 mg/ml), streptomycin sulphate (1 mg/ml), human transferrin (2.5 µg/ml), selenium (4 ng/ml), human insulin (10 ng/ml), rhFSH (1 ng/ml), ascorbic acid (50 µg/ml), Kit Ligand (10 µg/ml) & recombinant activin-A (100 ng/ml)). FSH concentration was adjusted as isolated follicle culture progressed. 1 ng/ml FSH for the first 48 hours increasing to 10 ng/ml for a further 96 hours with 100 ng/ml estradiol. If follicles remained in culture for 8 days FSH was increased to 100 ng/ml with estradiol 1 µg/ml.

Follicles were cultured individually for a further six days at 37° C. in humidified air with 5% $CO_2$, with half of the culture medium being replaced every other day (e.g. on day 2 and day 4). By day 4 significant growth is observed in isolated follicles and antral cavity formation may have occurred. On day 6 those follicles that have reached a minimum diameter of 200 µm were prepared for removal of the oocyte-cumulus cell complex to allow further oocyte development.

Release of Oocyte Cumulus Complexes (OCCs) from Intact In-Vitro Grown Follicles for Further Culture on Membranes In vitro grown follicles having a minimum diameter of 200 µm may or may not have formed an antral cavity. Release of OCCs from intact follicles must ensure the integrity of the OCC. Loss of contact between the oocyte and its surrounding somatic cumulus cells will result in degeneration of the oocyte and failure of in vitro maturation. Once released from the follicles it is critical that the OCCs are transferred onto a supportive membrane to maintain the physical contact between the oocyte and surrounding cells and ensure correct complex architecture during completion of oocyte growth.

In vitro grown follicles were transferred from culture medium into a glass petri dish containing pre-warmed holding medium (Leibovitz (L-15) medium with human serum albumin (0.3% by weight), sodium pyruvate (2 mM), L-glutamine (2 mM), benzyl penicillin (75 µg/ml), streptomycin sulphate (50 µg/ml)) using a graduated plastic pastette. Follicles were held using fine forceps and examined under light microscopy to determine the presence of an antral cavity.

If an antral cavity was present the basal lamina of the follicle that forms part of the wall of the antral cavity was punctured using a 25 gauge needle, releasing follicular fluid containing the OCC into the petri dish. On release, the OCCs were immediately removed from the holding medium within the petri dish into pre-warmed OCC holding medium (Leibovitz (L-15) medium with human serum albumin (0.3% by weight), sodium pyruvate (2 mM), L-glutamine (2 mM), benzyl penicillin (75 µg/ml), streptomycin sulphate (50 µg/ml)) using pulled glass pipettes.

If no antral cavity is visible, the basal lamina of the follicle was punctured gently several times, taking care to puncture the basal lamina only. The follicle was gently stretched using two 25 gauge needles until the basal lamina was ruptured and the inner cells were exposed. Using a pulled glass pipette the inner cells were gently drawn back and forth until the OCC was detached from the follicle. The OCC was removed from the holding medium into the pre-warmed OCC holding medium using a pulled glass pipette.

Using pulled glass pipettes, OCCs were transferred from the OCC holding medium onto track-etched nucleopore membranes in 300 µL of OCC culture medium (McCoys 5A HEPES modified medium with human serum albumin (0.1% by weight), sodium pyruvate (2 mM), L-glutamine (3 mM), kanamycin sulphate (0.08 mg/ml), human transferrin (2.5 µg/ml), selenium (4 ng/ml), human insulin (10 ng/ml), FSH (100 ng/ml), IGF-1 (200 ng/ml), estradiol (1 µg/ml) & EGF (100 ng/ml)) in 4-well culture plates, a maximum of six complexes per membrane. It is critical that complexes containing oocytes of a similar diameter are cultured together on the same membrane to ensure that oocyte development, cumulus cell expansion and subsequent in vitro maturation is not comprised.

The position of every complex was noted on each membrane and measurements of the individual oocyte diameters and each cumulus spread were recorded. OCCs were then incubated at 37° C. in humidified air with 5% $CO_2$.

Half the OCC culture medium was replaced every second day concomitant with oocyte diameter and cumulus expansion measurements. The duration of OCC culture was dependent on oocyte diameter to ensure that the mean oocyte diameter exceeds 100 µm.

When the oocyte diameters are >100 µm the membranes were removed from the OCC culture medium using fine forceps and placed into 24-well culture plates, one membrane per well, allowing the membranes to adhere to the base of the well before carefully adding 30 µL of oocyte maturation media per complex.

Oocyte maturation media is a mixture of 2XTCM, solution B, solution C, MQ $H_2O$ mixed in the ratio (ml) 25:5:0.3:19.7 respectively, with an osmolarity between 280-300 mOsM, and at pH 7.3-7.4. 2XTCM comprises 20% solution TCM199, 0.01% by weight kanamycin sulphate, 0.04% by weight L-glutamine, Solution B comprises 2.1% by weight $NaHCO_3$ in $H_2O$ with an osmolarity between 430-440 mOsM, and Solution C comprises 0.36% by weight pyruvic acid solution (MQ $H_2O$) with an osmolarity between 55-60 mOsM. All water used was ultrapure of Type 1, such as Milli Q (MQ) water, and the media was filtered before use. 4.5 ml of the resulting maturation medium was diluted with 0.5 ml of human serum albumin and rhFSH (0.5 µg/ml), estradiol (1 µg/ml) and Luteinising Hormone (5 µg/ml) were added.

The maturation medium is covered with filtered mineral oil and the plates incubated for 22-28 hours at 38° C. in humidified air with 5% $CO_2$. Expulsion of the 1st polar body was visualised by light microscopy and used as the determinant as confirmation of meiotic resumption.

Once meiotic resumption is confirmed, the oocytes are ready for use in in vitro fertilization.

3 Isolated Follicle Culture Medium

McCoys 5A HEPES modified medium with bovine serum albumin (0.1% by weight), L-glutamine (3 mM), benzyl penicillin (1 mg/ml), streptomycin sulphate (1 mg/ml), bovine transferrin (2.5 µg/ml), selenium (4 ng/ml), bovine insulin (10 ng/ml), *FSH (1 ng/ml), ascorbic acid (50 µg/ml), Kit Ligand (10 µg/ml) & recombinant activin-A (100 ng/ml).

*FSH concentration should be adjusted as isolated follicle culture progresses. 1 ng/ml FSH for first 48H increasing to 10 ng/ml for a further 96H with 100 ng/ml estradiol. If follicles remain in culture for 8 days FSH is increased to 100 ng/ml with estradiol 1 µg/ml.

NB The addition of bovine serum, bpV(HOpic), 740-P, GDF-9 & BMP15 individually or in combination is contra-indicated in isolated follicle culture. FSH concentration should be adjusted as described to maintain oocyte somatic cells contact.

4 Bovine Oocyte Cumulus Complex Culture Medium

McCoys 5A HEPES modified medium with bovine serum albumin (0.1% by weight), sodium pyruvate (2 mM), L-glutamine (3 mM), kanamycin sulphate (0.08 mg/ml), bovine transferrin (2.5 µg/ml), selenium (4 ng/ml), bovine insulin (10 ng/ml), FSH (100 ng/ml), IGF-1 (200 ng/ml), estradiol (1 µg/ml) & EGF (100 ng/ml).

Bovine Oocyte Maturation System

The system comprises bovine oocyte holding and bovine oocyte maturation media. These are composites of several solutions which must be prepared freshly before use. All water must be ultrapure of Type 1, such as Milli Q (MQ)

TABLE 2

Human and bovine follicle maturation in multi-step culture system.

| Species | IVG Follicles | Final Diameter (µm +/− SEM) | No. Antral Follicles (%)* | No. OCCs Released (%)* | No. MII: 1st Polar Body Extruded (%)* |
|---|---|---|---|---|---|
| Human | 145 | 213 +/− 2.7 | 42 (28.9) | 35 (24.1) | 17 (11.7) |
| Bovine | 172 | 238 +/− 1.9 | 81 (47.1) | 71 (41.3) | 30 (17.4) |

*(%) refers to follicles and OCCs progressing through the complete in vitro system as a percentage of the total number of IVG follicles. Presence of an antrum can be determined by light microscopy in intact follicles or by microscopic inspection of the OCCs following rupture of the basal lamina. Over 40% of oocytes released from either IVG human or bovine follicles will progress to metaphase II (MII).

Application to Bovine Systems

The above methods may be carried out on bovine ovarian tissue samples using the following media:

In Vitro Bovine Ovarian Follicle Activation, Development & Bovine Oocyte Maturation 1 Tissue Holding Medium Leibovitz (L-15) medium with bovine serum albumin (0.3% by weight), sodium pyruvate (2 mM), L-glutamine (2 mM), benzyl penicillin (75 µg/ml), streptomycin sulphate (50 µg/ml).

2 Micro-Cortex Culture Medium

McCoys 5A HEPES modified medium with bovine serum albumin (0.1% by weight), L-glutamine (3 mM), benzyl penicillin (1 mg/ml), streptomycin sulphate (1 mg/ml), bovine transferrin (2.5 µg/ml), selenium (4 ng/ml), bovine insulin (10 ng/ml), FSH (1 ng/ml) & ascorbic acid (50 µg/ml).

NB The addition of bovine serum, activin-A, bpV (HOpic), 740-P, GDF-9 & BMP15 individually or in combination is contra-indicated in micro-cortex culture. Tissue viability can be adversely affected by alteration of the FSH concentration. It is advised that antibiotic insulin combination products are avoided.

water, for example. Following optimising of osmolarity and pH, medium can be stored at −20° C. prior to the addition of serum.

Bovine Oocyte Holding Medium

2XTCM 199, solution A, solution B, MQ $H_2O$ in the ratio (ml) 25:3:1:21 respectively Osmolarity 280-300 mOsM*, pH 7.3-7.4*

*Osmolarity and pH MUST be within shown limits

To use: dilute 9 ml of holding medium with 1 ml of bovine serum, warm before use.

2XTCM 199

20% solution TCM199, 0.01% by weight kanamycin sulphate, 0.04% by weight L-glutamine Solution A 3% HEPES—free acid, 3.25% by weight HEPES sodium salt in $H_2O$ Osmolarity 380-385 mOsM*

*Osmolarity must be within shown limits

Solution B 2.1% by weight $NaHCO_3$ in $H_2O$

Osmolarity 430-440 mOsM*

*Osmolarity must be within shown limits

Filter holding medium before use

Bovine oocyte maturation medium

2XTCM, solution B, solution C, MQ H$_2$O in the ratio (ml) 25:5:0.3:19.7 respectively Osmolarity 280-300 mOsM*, pH 7.3-7.4*

*Osmolarity and pH must be within shown limits.

Solution C 0.36% by weight pyruvic acid solution (MQ H$_2$O)

Osmolarity 55-60 mOsM*

*Osmolarity and pH must be within shown limits.

Filter before use. Medium can be stored at −20° C. prior to the addition of serum and hormones.

To use; dilute 4.5 ml of bovine maturation medium with 0.5 ml of bovine serum & add FSH (0.5 μg/ml), estradiol (1 μg/ml) and Luteinising Hormone (5 μg/ml). Warm to 38° C. before use in humidified air with 5% CO$_2$.

REFERENCES

Eppig J. J., O'Brien M. J. (1996) Development in vitro of mouse oocytes from primordial follicles. *Biol Reprod;* 54: 197-207.

O'Brien M. J., Pendola J. K., Eppig J. J. (2003) A revised protocol for in vitro development of mouse oocytes from primordial follicles dramatically improves their developmental competence. *Biol Reprod;* 68: 1682-1686.

Telfer E. E., McLaughlin M. (2012) Strategies to support human oocyte development in vitro *Int. J. Dev. Biol.* 56: 901-907.

Telfer E. E., McLaughlin M., Ding C., Thong K. J. (2008) A two-step serum-free culture system supports development of human oocytes from primordial follicles in the presence of activin. *Hum Reprod;* 23: 1151-1158.

McLaughlin M., Telfer E. E. (2010) Oocyte development in bovine primordial follicles is promoted by activin and FSH within a two-step serum-free culture system. *Reproduction* 139: 971-978.

Ma I., Allan A. L. (2011) The role of human aldehyde dehydrogenase in normal and cancer stem cells. *Stem Cell Rev and Rep.* 7:292-306.

The invention claimed is:

1. A method of preparing ovarian tissue for primordial follicle growth comprising the steps:
   providing an ovarian tissue sample comprising cortical tissue and stromal tissue;
   removing damaged tissue from the ovarian tissue, sample where present;
   removing excess stromal tissue from the ovarian tissue sample where present; and then
   mechanically stretching the ovarian tissue sample along at least one dimension of the ovarian tissue sample, such that the size of the ovarian tissue sample along the at least one dimension is increased by at least 10%.

2. The method according to claim 1, wherein the ovarian tissue sample is mechanically stretched along multiple dimensions of the ovarian tissue sample.

3. The method according to claim 1, wherein the thickness of the layer of stromal tissue is reduced to between 1 and 5 mm after the step of removal of excess stromal tissue from the ovarian tissue sample.

4. The method according to claim 3, wherein the thickness of the layer of stromal tissue is reduced to 3 mm after the step of removal of excess stromal tissue, from the ovarian tissue, sample.

5. The method according to claim 1, wherein the ovarian tissue sample is cut into a plurality of smaller ovarian tissue fragments after the step of mechanically stretching the ovarian tissue sample.

6. The method according to claim 1, wherein the cortical tissue within the ovarian tissue sample forms a cortical surface on a first side of the ovarian tissue sample and the stromal tissue forms a stromal surface on a second side of the ovarian tissue, opposed to the first side.

7. The method according to claim 6, wherein the surface area of the cortical surface is at least 1 to 2 times the surface area of the stromal surface after the step of mechanically stretching the ovarian tissue sample.

8. The method according to claim 7, wherein the surface area of the cortical surface is about 1.5 times the surface area of the stromal surface after the step of mechanically stretching the ovarian tissue sample.

9. The method according to claim 1, wherein the cortical tissue comprises a population of endogenous ovarian follicles, and wherein further endogenous ovarian follicles within the population of endogenous ovarian follicles with a diameter greater than 80 μm are mechanically removed from the ovarian tissue.

10. The method according to claim 1, wherein the ovarian tissue sample is cultured in a serum-free media comprising follicle stimulating hormone (FSH) for at least twenty four hours.

11. The method according to claim 10, wherein the serum-free media may comprise between 0.5 ng/ml to 2.5 ng/ml FSH.

12. The method according to claim 10, wherein a population of isolated ovarian somatic support cells are introduced into the cortical tissue of the ovarian tissue sample after culturing for at least twenty four hours.

13. The method according to claim 12, wherein the isolated somatic support cells are DDX4 negative.

14. The method according to claim 12, wherein the ovarian tissue sample are then cultured for a further period of at least four days after the step of introducing the population of isolated ovarian somatic support cells.

* * * * *